United States Patent
Blanton et al.

(10) Patent No.: US 8,101,377 B2
(45) Date of Patent: Jan. 24, 2012

(54) PROTEIN HYDROLYSATES AND METHOD OF MAKING

(75) Inventors: Madison V. Blanton, Littleton, CO (US); Richard K. Merrill, Highlands Ranch, CO (US); Shannan E. Guck, Windsor, CO (US)

(73) Assignee: Leprino Foods Company, Denver, CO (US)

( * ) Notice: Subject to any disclaimer, the term of this patent is extended or adjusted under 35 U.S.C. 154(b) by 1122 days.

(21) Appl. No.: 11/619,957

(22) Filed: Jan. 4, 2007

(65) Prior Publication Data

US 2007/0172579 A1 Jul. 26, 2007

Related U.S. Application Data

(60) Provisional application No. 60/756,456, filed on Jan. 4, 2006.

(51) Int. Cl.
*C12P 21/06* (2006.01)

(52) U.S. Cl. ......... 435/68.1; 435/41; 530/832; 530/833; 530/366

(58) Field of Classification Search .................. None
See application file for complete search history.

(56) References Cited

U.S. PATENT DOCUMENTS

| | | | |
|---|---|---|---|
| 4,482,574 A | 11/1984 | Lee | |
| 6,183,802 B1 | 2/2001 | Silva et al. | |
| 6,395,508 B1 | 5/2002 | Shimamura et al. | |
| 6,589,574 B2 | 7/2003 | Swamylingappa et al. | |
| 6,919,314 B1 | 7/2005 | Schlothauer et al. | |
| 7,148,034 B2 * | 12/2006 | Schlothauer et al. | 435/68.1 |
| 2003/0099753 A1 | 5/2003 | Yang | |
| 2004/0166203 A1 | 8/2004 | Gautam et al. | |

FOREIGN PATENT DOCUMENTS

| | | |
|---|---|---|
| EP | 0 065 663 A1 | 12/1982 |
| WO | WO 93/04593 A1 | 3/1993 |
| WO | WO 01/28353 | 4/2001 |
| WO | WO 2005/089565 A1 | 9/2005 |

OTHER PUBLICATIONS

Liaset et al., Process Biochemistry, 2002, vol. 37, p. 1263-1269.*
Kristinsson et al., Critical Reviews in Food Science and Nutrition, 2000, vol. 40. No. 1, p. 43-81.*
Saha et al., Biotechnology Advances, 2001, vol. 19, p. 355-370.*
Britten et al., J dairy Science, 1994, vol. 77, p. 676-684.*
Salaun et al., International Dairy Journal, 2005, vol. 15, p. 95-109.*
Margesin et al. , Journal of Biotechnology, 1994, vol. 33, p. 1-14.*
Poulsen et al., Electrophoresis, 1986, vol. 7, p. 166-171.*
De Wit, J.N, 1990, J Dairy Science, vol. 73, p. 3602-3612.*
Miller et al., Journal of Food Science, 1983, vol. 48, Issue 1, Abstract.*
Kumar, R., et al., "Enzymatically Modified Soy Protein, Part I. Thermal Behaviour," Journal of Thermal Analysis and Calorimetry, 2004, vol. 75, No. 3, pp. 727-738.

* cited by examiner

*Primary Examiner* — Kade Ariani
(74) *Attorney, Agent, or Firm* — Kilpatrick Townsend & Stockton LLP

(57) ABSTRACT

Methods of making protein hydrolysates are described. The methods may include the steps of providing a solution comprising protein, and adjusting a pH of the solution to about 10.4 or more to form a basic protein solution. Additional steps may include adding a protease enzyme to the basic protein solution that converts at least a portion of the protein to protein hydrolysates. Protein hydrolysate compositions and water-soluble food additives are also described. The additives may include a mixture of protein hydrolysates formed by protein hydrolysis of a protein substrate. The protein hydrolysates may have an average molecular weight of about 2000 to about 10,000 Daltons.

29 Claims, 10 Drawing Sheets

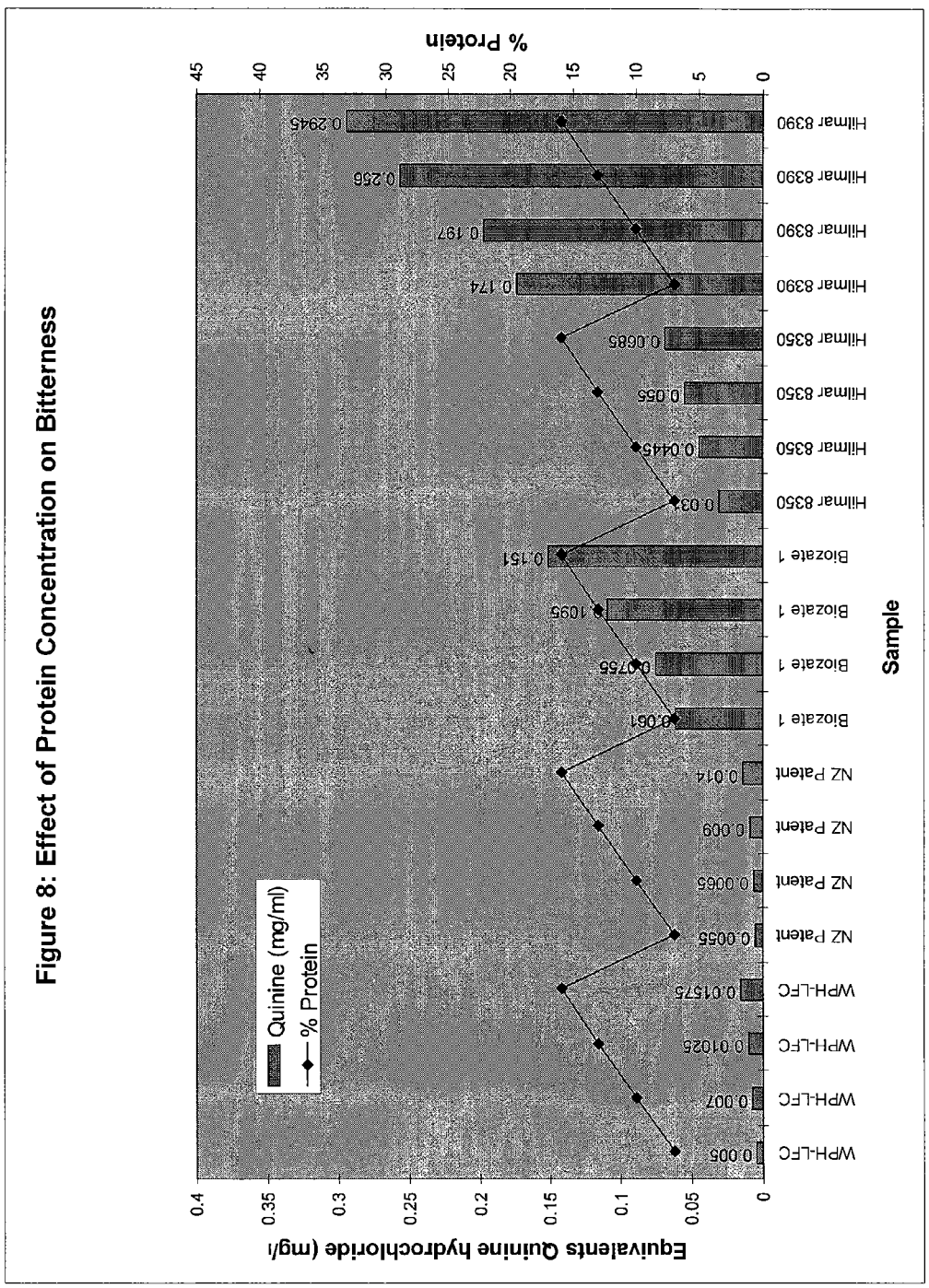

PROTEIN HYDROLYSATES AND METHOD OF MAKING

CROSS-REFERENCES TO RELATED APPLICATIONS

This application claims priority to U.S. Provisional App. No. 60/756,456, filed Jan. 4, 2006, and titled "PROTEIN HYDROLYSATES AND METHOD OF MAKING", the entire contents of which are herein incorporated by reference for all purposes.

BACKGROUND OF THE INVENTION

For years, nutritionists have recommend foods that are high in protein and low in saturated fat. These recommendations often go unheeded by consumers who find a diet of high-fat, sugar-concentrated pastries, candy bars, and soft drinks an irresistible alternative to hard-boiled egg whites, kidney beans, and skim milk. To try and reconcile the sometimes conflicting goals between foods that are healthy and foods that taste good, manufacturers replace some of the less healthy substances in popular foods with healthier ingredients. For example, some of the saturated fats and sugars in conventional ice cream can be replaced with proteins and sugar substitutes that make the ice cream less caloric, and less concentrated in fats and processed sugar. Substituting proteins for fats and carbohydrates has even been extended to foods such as pastas and candy bars.

A significant source of protein used for ingredient substitution comes from the dairy industry, where large quantities of proteins like whey and casein can be separated from dairy milk. Whey protein, for example, is a natural by-product of cheesemaking that has value added uses as a protein substitute. But the native forms of these proteins have physical and organoleptic properties that often make them poor substitutes for fats and carbohydrates. The native proteins also tend to be hygroscopic and soak up the moisture in their vicinity. As a result, solid foods can taste dry, and even liquid drinks can have a chalky aftertaste.

Incorporation of proteins, principally whey proteins, have faced many problems thus preventing their incorporation into food products as the major protein source. For example, whey protein incorporation in to shelf stable beverages is limited due to instability of the protein during heat treatment, resulting in precipitation and/or gelling of the whey protein. Additionally, incorporation of whey protein into nutritional bars leads to bars with shorter shelf life, primarily due to premature hardening of bars compared to bars that have little or no whey protein.

To make dairy proteins a more appealing food substitute, the large native proteins are hydrolyzed into smaller protein fragments (called protein hydrolysates) with protease enzymes. The smaller protein fragments are generally more soluble in water, and less hygroscopic than the starting protein. They can be dissolved in beverages to make concentrated protein drinks, and added to solid foods to impart a smooth, less chalky taste. But cutting the native proteins into fragments also has a significant drawback: Protein hydrolysates are commonly very bitter tasting, and not all protein hydrolysates are heat stable.

The increasing bitterness is attributed to the increased ability of the protein fragments to reach bitter taste receptors on a person's taste buds. Bitterness is tasted when hydrophobic amino acid side groups in the protein fragment can reach these receptors. The large native proteins are so bulky that the bitterness activating side groups have trouble maneuvering to the bitterness receptors, so the native proteins taste bland instead of bitter.

The increased bitterness of protein hydrolysates is predictable enough for food scientists to quantify the relationship between bitterness and protein size by determining the mean hydrophobicity of the hydrolysate, known as its Q-value. The Q-value is calculated by counting the number of amino acid groups (n) that make up the protein hydrolysate, and summing the changes in the free energy for each amino acid group ($\Delta g$) as the protein dissolves in the person's mouth. An equation to calculate a protein hydrolysate's Q-value looks like:

$$Q = \frac{\sum \Delta g}{n}$$

The higher the Q-value the more likely the protein will taste bitter. Because the number of amino acid groups (n) is in the denominator of the Q-value equation, a smaller number of amino acid groups (i.e., a smaller protein) gives a higher Q-value, increasing the chance that the protein will taste bitter. Studies show that most protein hydrolysates with Q-values above 1400 are noticeably bitter, while those with Q-values below 1300 do not taste bitter.

Another procedure to evaluate bitterness in protein hydrolysates is comparing aqueous solutions of the hydrolysates with increasing concentrations of a standard bitter substance such as quinine hydrochloride of caffeine. When the hydrolysates taste equally bitter as a particular concentration of the standard, they are said to have an equivalent bitterness to that concentration level of the standard. Hydrolysate bitterness can be expressed quantitatively as the equivalent to a specific concentration (or concentration range) of a bitter standard solution.

Food and beverage makers have tried several approaches to deal with the bitter taste of protein hydrolysates. These include attempts to mask the bitterness with sweet tasting sugars, and other flavor agents. Flavor agents that cancel the proteins' bitter taste while preserving desired food flavors can be expensive and difficult to develop, and typically do a poor job masking bitter flavors. Use of debittering enzymes during hydrolysis or filtration of the hydrolyzed protein have also been employed to reduce bitterness, although without much success.

In another approach, food makers have tried to cut the protein hydrolysates into smaller peptide units, sometimes even breaking down the protein into individual amino acids. Extensive hydrolysis of proteins down to these sizes has been shown to reduce the bitterness tasted in the larger hydrolysates. But the bitterness is usually replaced with soapy and brothy off-flavors from the peptides that are only slightly more palatable than the bitter tasting hydrolysates. Moreover, bitter flavor and aftertaste are often still noticeable even after the hydrolysis.

Clearly, a large and mostly untapped market can be realized if large native proteins such as dairy milk proteins can be converted into palatable and process stable protein hydrolysates. Not only would such conversion processes create a valuable market for dairy protein by-products like whey, they would also enable consumers to make a seamless transition to healthier foods that are still enjoyable to eat. These processes of making useful, good-tasting protein hydrolysates, as well as various foods and beverages made from them, are described by the present invention.

BRIEF SUMMARY OF THE INVENTION

Embodiments of the invention relate to methods of making protein hydrolysates. The methods may include the steps of providing a solution that includes protein, and adjusting the pH of the solution to about 10.4 or more to form a basic protein solution. The methods may also include adding a protease enzyme to the basic protein solution that converts at least a portion of the protein in the solution to protein hydrolysates.

Embodiments of the invention further include protein hydrolysate compositions made by the above-described method. The compositions are heat stable at a temperature of about 190° F. or more for about 5 minutes or more. The compositions may also have a bitterness equivalent of about 0.03 mg/ml or less of quinine hydrochloride.

Embodiments of the invention also include additional methods of making protein hydrolysates. These methods may include the steps of providing a solution that includes protein, and cooling the protein solution to about 50° F. or less. The methods may also include adjusting the pH of the solution to about 8 or more, and adding a protease enzyme to the cooled, basic protein solution that converts at least a portion of the protein to protein hydrolysates.

Embodiments of the invention still also include further methods of making protein hydrolysates. These methods may include the steps of providing a solution that includes protein, and adjusting the pH of the solution to about 8 or more to form a basic protein solution. The basic solution may be mixed for about 30 minutes or more, and a protease enzyme may be added to the basic protein solution. The protease enzyme converts at least a portion of the protein to protein hydrolysates.

Embodiments of the invention also further include more methods of making protein hydrolysates. The methods may include the steps of providing a solution that includes protein, and adjusting the pH of the solution to about 8 or more. The methods may further include adding a non-alkaline protease enzyme to the basic protein solution that converts at least a portion of the protein to protein hydrolysates.

Embodiments of the invention yet still further include still more methods of making whey protein hydrolysate. The methods may include the steps of providing a solution comprising about 10% by wt. of whey protein concentrate, and cooling the solution to about 45° F. Further steps may include adjusting the pH of the solution to about 10.4 by adding aqueous sodium hydroxide to the solution, mixing the solution for 30 minutes at the 45° F. temperature, and adding a *Bacillus* sourced protease enzyme (e.g., Protamex® (Novozymes A/S, Krogshoejvej 36, 2880 Badsvaerd Denmark)) to the solution, wherein the protease enzyme is added in an amount of about 0.5% by weight of the whey protein concentrate. The solution may be mixed either for 24 hours or until the pH drops to about 9.5 or less, where the protease enzyme converts at least a portion of the whey protein to whey protein hydrolysates. Additional steps may include incubating the solution at about 90° F. to about 140° F. for about 30 to about 300 minutes, heating the solution to about 180° F. for about 10 minutes before removing water from the solution, and then drying the solution to form a solid composition comprising the whey protein hydrolysate.

Embodiments of the invention yet still further include still more methods of making whey protein hydrolysate. The methods may include the steps of providing a solution comprising about 10% by wt. of whey protein concentrate, and cooling the solution to about 45° F. Further steps may include adjusting the pH of the solution to about 10.4 by adding aqueous sodium hydroxide and tripotassium phosphate to the solution, mixing the solution for 30 minutes at the 45° F. temperature, and adding a *Bacillus* sourced protease enzyme (e.g., Protamex® (Novozymes A/S, Krogshoejvej 36, 2880 Badsvaerd Denmark)) to the solution, wherein the protease enzyme is added in an amount of about 0.5% by weight of the whey protein concentrate. The solution may be mixed either for 24 hours or until the pH drops to about 9.5 or less, where the protease enzyme converts at least a portion of the whey protein to whey protein hydrolysates. Additional steps may include incubating the solution at about 90° F. to about 140° F. for about 30 to about 300 minutes, heating the solution to about 180° F. for about 10 minutes before removing water from the solution, and then drying the solution to form a solid composition comprising the whey protein hydrolysate.

Embodiments of the invention may also include water-soluble food additives that may include mixtures of protein hydrolysates formed by enzyme hydrolysis of a protein substrate. The protein hydrolysates in the mixture have an average molecular weight of about 2000 to about 10,000 Daltons.

Embodiments of the invention may further include water-soluble food additives made from mixture of protein hydrolysates formed by enzyme hydrolysis of a protein substrate. The protein hydrolysates in the mixture have an average Q value of about 1300 or less.

Embodiments of the invention may further include water-soluble food additives made from mixture of protein hydrolysates formed by enzyme hydrolysis of a protein substrate. The protein hydrolysates in the mixture have a quinine equivalent of less than 0.003 mg/ml quinine hydrochloride.

Embodiments of the invention may further include water-soluble food additives made from mixture of protein hydrolysates formed by enzyme hydrolysis of a protein substrate. The protein hydrolysates in an aqueous solution comprising about 7% protein and having a quinine equivalent of less than 0.03 mg/ml quinine hydrochloride.

Embodiments of the invention may further include water-soluble food additives made from mixture of protein hydrolysates formed by enzyme hydrolysis of a protein substrate. The protein hydrolysates in an aqueous solution comprising about 7% protein and being heat stable at about 180° F. to about 300° F. for about 1 second to about 50 minutes.

Embodiments of the invention may also include methods of making a protein added confectionery. The methods may include the steps of mixing a sweetener and a solid fat into a first mixture, and heating the first mixture until the solid fat begins to melt. The methods may also include adding a compound comprising protein hydrolysates to the melted mixture, where the protein hydrolysates have an average molecular weight of about 2000 to about 10,000 Daltons. Additional ingredients may also be added such as a liquid dairy product to the melted mixture to form a protein fortified confectionery mixture. The methods may further include cooking the confectionery mixture into the confectionery.

Embodiments of the invention may still further include methods of making a protein fortified beverage. The methods may include mixing water and protein hydrolysates to the first mixture, where the protein hydrolysates have an average molecular weight of about 2000 to about 10,000 Daltons. The methods may also include adding one or more additional ingredients to the water to form a raw beverage, and heating the raw beverage to form the protein fortified beverage.

Embodiments of the invention may also further include compositions of protein hydrolysates. The compositions may be heat stable at a temperature of about 190° F. or more for about 5 minutes or more. They may also have a bitterness equivalent of about 0.03 mg/ml or less of quinine hydrochloride.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

FIG. 8 shows a graph of the effect of protein concentration on bitterness for various protein hydrolysates samples.

DETAILED DESCRIPTION OF THE INVENTION

Figure 1:
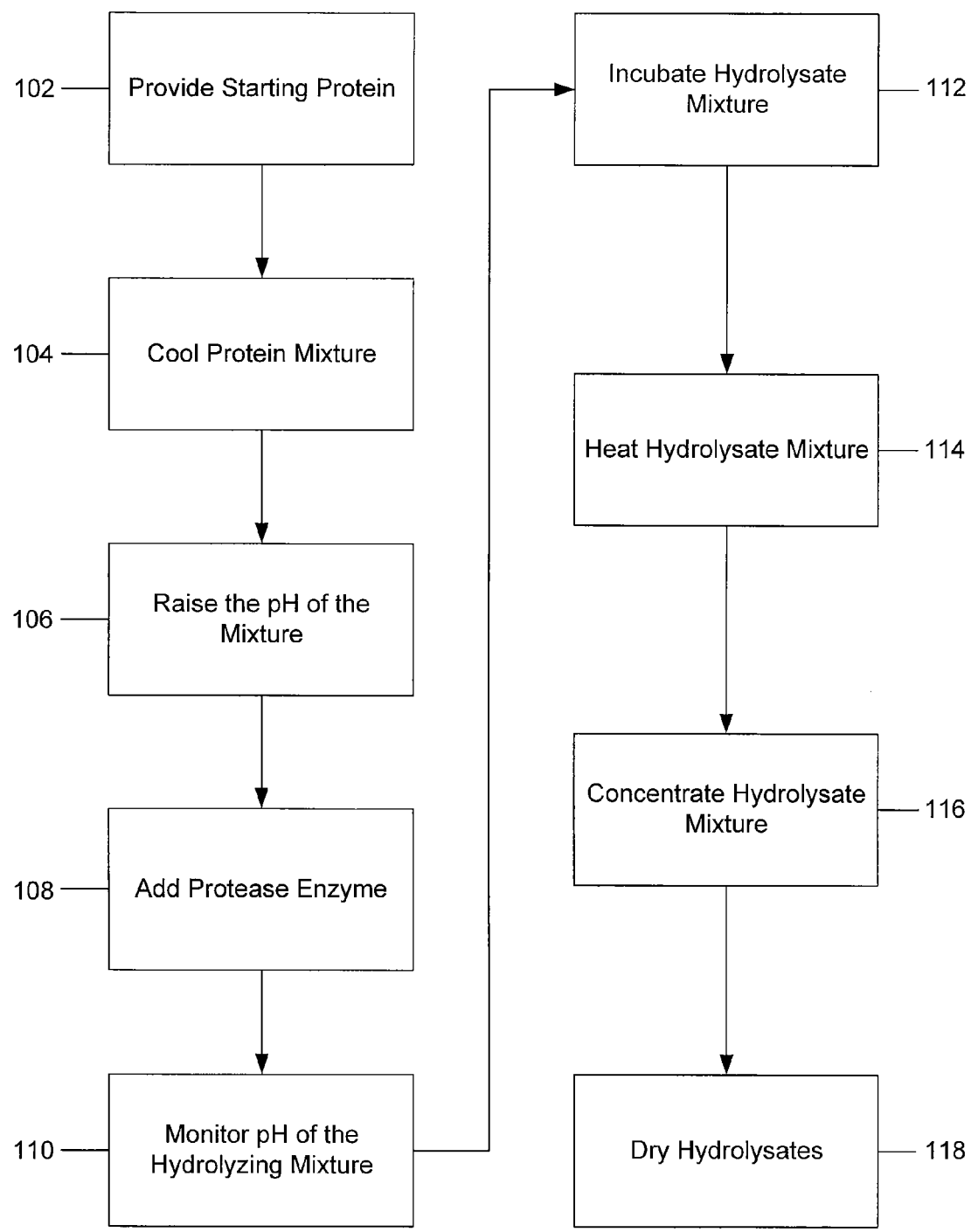
FIG. 1 is a flowchart that provides an overview of steps in a process of making protein hydrolysates according to embodiments of the invention.

Mixtures of protein hydrolysates are described that have size profiles that make them well suited as protein additives and ingredient substitutes in popular foods and beverages. The average size of the hydrolysates fall within a range where they are small enough to have good solubility and hygroscopic properties, but large enough not to taste bitter. These hydrolysates may be derived from whole native proteins in a highly basic aqueous solutions (e.g., solutions with a pH greater than 10). Proteolytic enzymes in the basic protein solution cut the proteins into the protein hydrolysates.

Temperature, pH and other parameters of the hydrolysis processes are controlled to keep the proteolytic enzymes from over hydrolyzing the native proteins. The processes may be described as a partial proteolysis (also called a partial protein hydrolysis) of the native proteins, because under different conditions the hydrolysate products are usually capable of being cut into even smaller protein fragments. The typical protein hydrolysate produced is large enough to have problems reaching the bitterness receptors on a person's taste buds, but not so large that they significantly gel, clump, precipitate, thicken, or harden when added to foods and beverages.

The Protein Hydrolysates

The protein hydrolysates may be made by the enzymatic hydrolysis of native food proteins, such as soy proteins, and dairy proteins (e.g., whey, casein), wheat proteins, canola proteins, corn proteins, vegetable proteins, grain proteins, and animal proteins, among other kinds of proteins. Numerically, the protein hydrolysates may have an average weight of about 2000 to about 10,000 Daltons. The protein hydrolysates may have about 67% or less of the proteins having a weight below 6000 Daltons. Embodiments also include protein hydrolysates may have an average weight of about 2000 to about 5000 Daltons. In general, smaller protein hydrolysates tend to have larger Q-values, indicating a higher probability of having a bitter taste. The greater the percentage of the hydrolysate products having smaller molecular weights (e.g., less than about 2000 Daltons) the greater the chance a consumer will notice a bitter taste. As the molecular weight profile data below shows, hydrolysate products with about 45% or less of protein hydrolysates weighing less than 2000 Daltons, have little or no detectable bitterness.

The percentage of hydrolysates with high molecular weights may also be controlled to avoid overloading the product with proteins that are prone to aggregation upon heating. The average molecular weight hydrolysate in the protein hydrolysate product has solubility in water that is significantly higher than the native protein from which it was made. This solubility refers to the quantity of the hydrolysate that remains dissolved in water after heating. The solubility of any solute (including the hydrolysates) can vary depending on solution conditions such as temperature, pH, ionic strength, presence of minerals, and the type of solvent, among other conditions. For proteins, the dependence of solubility on temperature is additionally complicated because some proteins can undergo chemical denaturation at even moderate temperatures, such as 104-122° F.

In protein denaturation, a protein's shape, size and physical properties are changed without breaking the covalent bonds between the amino acids that define the primary structure of the protein. A familiar example of protein denaturation occurs when boiling an egg: The heat from the boiling water denatures the proteins in the clear and runny raw egg white into an opaque, rubbery solid. The water isn't hot enough to break the covalent bonds of the amino acids into smaller peptides, but it does provide enough energy to reshape and entangle the egg proteins into a hard-boiled egg.

In most instances, protein denaturation reduces the solubility of the protein in water. The changes in shape that occur during denaturation often expose more of the protein's non-polar, hydrophobic functional groups to the external environment. This reduces the ability of water, a polar solvent, to surround the protein molecule and bind to it. In addition, denaturation often unwinds the protein, and its exposed branches and strands get entangled with other proteins. The aggregation of the proteins can quickly snowball, causing the proteins to coagulate into a gel and/or solidify into a suspension or precipitate.

Protein denaturation and its effect on solubility present unusual challenges for food and beverage makers. Food ingredients like salts and sugars get more soluble as the temperature is increased. They don't clump together or precipitate during heating and pasteurizing steps in the food preparation process. But proteins (including large native proteins from soy, milk, and other foods) have the opposite behavior, and tend to separate out of the food when the temperature is raised. The protein added product develops a gummy or gritty texture that most consumers find unappealing, if not unpalatable.

Because protein hydrolysates are smaller than the original proteins they're cut from, they generally do not denature or absorb water to the same extent. They usually have fewer hydrophobic groups being exposed, and they do not have as many branches and strands that can unwind and become entangled with neighboring hydrolysates. The problems caused by the denaturation of native food proteins are often muted in their hydrolysates, even when the hydrolysates are still relatively large molecules that weigh from 2000 to 10000

Daltons or more. Consequently, even partial enzymatic hydrolysis that hydrolyzes the original protein by only 3 to 8% of complete hydrolysis may still increase the solubility of the protein hydrolysates by 50% to 80% or more compared to the whole protein. Though it should be noted that partially hydrolyzed proteins may still gel and/or precipitate when heated. The molecular weight profile data below shows hydrolysate products with about 33% or less of protein hydrolysates weighing more than 5000 Daltons, produce little or no detectable grittiness at temperatures used to make and heat treat protein added foods.

Protein denaturation may also increase the hygroscopic properties of native food proteins (i.e., the denatured proteins tend to absorb more water). This can affect the palatability of both beverages and solid foods: In beverages and other liquid foods, hygroscopic proteins can draw water away from the drinker's tongue to cause a dry, chalky aftertaste. In solid foods, hygroscopic proteins can soak up moisture and leave the food with a dry, stale texture and mouthfeel. Protein hydrolysates are generally less hygroscopic than the starting protein, and significantly less hygroscopic than the denatured protein.

Exemplary Processes of Making Protein Hydrolysates

Protein hydrolysates may be made by the enzymatic hydrolysis (i.e., proteolysis) of a starting protein. The hydrolysis environment may include an aqueous mixture of the starting protein and protease enzymes, where temperature, pH and other mixture parameters are controlled to produce a protein hydrolysates product according to the invention. FIG. 1 is a flowchart that provides an overview of steps in a process 100 of making protein hydrolysates according to embodiments of the invention.

The protein hydrolysate production process 100 includes providing an aqueous mixture of the starting protein 102, which may include one or more native food proteins like soy, whey, casein, and/or other food proteins. The protein may be concentrated, with the starting protein making up 5% or more (by weight) of the overall mixture. The mixture may then be cooled 104 below room temperature (e.g., about 45° F.).

A base and/or sequestrant may be added to raise the pH of the mixture 106 to about 10 or more (e.g., a pH of about 10.4). The base may be a concentrated aqueous solution of a strong base such as sodium hydroxide (e.g., 40%, by wt., NaOH) that is poured into the native protein mixture. The sequestrant may be a concentrated aqueous solution of a compound that sequesters a cation in the mixture (e.g., calcium ions). Examples of sequestrants may include phosphates, pyrophosphates, diphosphates, triphosphates, polyphosphates, carbonates, and citrates. For example, the sequestrant may include one or more of disodium diphosphate, trisodium diphosphate, tetrasodium diphosphate, dipotassium diphosphate, tetrapotassium diphosphate, dimagnesium diphosphate, pentasodium triphosphate, pentapotassium triphosphate, sodium polyphosphate, potassium polyphosphate, ammonium polyphosphate, potassium tripolyphosphate, disodium phosphate, dipotassium phosphate, citric acid, lactobionic acid, phosphoric acid, tetrasodium pyrophosphate, sodium metaphosphate, sodium hexametaphosphate, tripotassium phosphate, trisodium citrate, trisodium phosphate, tripotassium citrate, disodium pyrophosphate, disodium ethyleneaminetetraacetate, sodium gluconate, sodium lactobionate, and/or sodium potassium tripolyphosphate. Additional examples of sequestrants include sodium hexametaphosphate, potassium tripolyphosphate, and/or tetrasodium pyrophosphate, among other sequestrants. The basic protein mixture may then be mixed for a period of time (e.g., 30 minutes to 12 hours) before adding the protease enzyme 108 to start hydrolyzing the protein. The protease enzyme may be an alkaline protease, an acid protease, or a neutral protease that can catalyze the protein hydrolysis at high pH (e.g., a pH range between 8 and 11).

When a protein is cleaved in the protease catalyzed hydrolysis reaction, one of the hydrolysis products is left with a carboxylic acid functional group. Formation of this acidic functional group lowers the pH of the mixture. As the protein hydrolysis progresses the pH of the mixture will continue decreasing, so monitoring the pH 110 can provide insight into the extent of the hydrolysis. For example, a change in the pH from about 10.4 to about 9.5 may signal that the hydrolysis has progressed to the point where the protein hydrolysates are near the desired molecular weight profile (e.g., median molecular weight in the range of about 2000 to about 5000 Daltons). When the mixture falls to the target pH, the low temperature hydrolysis reaction may be stopped.

Alternatively, the endpoint of the reaction may be time based. When relevant reaction conditions (like temperature, starting materials, pH, etc.) follow a predictable course during the reaction, the hydrolysate product composition over time may also be predictable. The reaction may be stopped at a time when the molecular weight profile of the hydrolysates nears the desired distribution. So, for example, the reaction can be timed from the addition of the protease enzymes to the starting protein mixture 108 until a predetermined time (e.g., 10 to 24 hours) when the hydrolysate product is closer to an average molecular weight and/or distribution profile of molecular weights according to embodiments of the invention.

This may be followed by an incubation stage 112 where the hydrolysis mixture is heated to an incubation temperature (e.g., about 90° F. to about 140° F.) for an incubation time (e.g., about 30 to about 300 minutes). Stopping the hydrolysis reaction may involve a high temperature stage 114, where the mixture is heated to a higher temperature (e.g., about 180° F.) for a shorter period of time (e.g., about 10 minutes) to inactivate the enzyme. Alternatively, the mixture may be heated to an even higher temperature (e.g., about 250° F.) for an even shorter period of time (e.g., about 5 seconds or more).

After the catalytic hydrolysis is finished, the hydrolysates mixture may be concentrated 116, before drying the final product 118. The mixture may be concentrated by, for example, filtering and/or evaporating water from the mixture. The bulk of the water may be removed from the mixture by heat, vacuum evaporation and/or filtration. The remaining hydrolysate distillate may be dried by a conventional drying process, such as spray drying, heated drying, and evaporation, among other processes.

Exemplary Apparatus for Making Protein Hydrolysates

Figure 2:
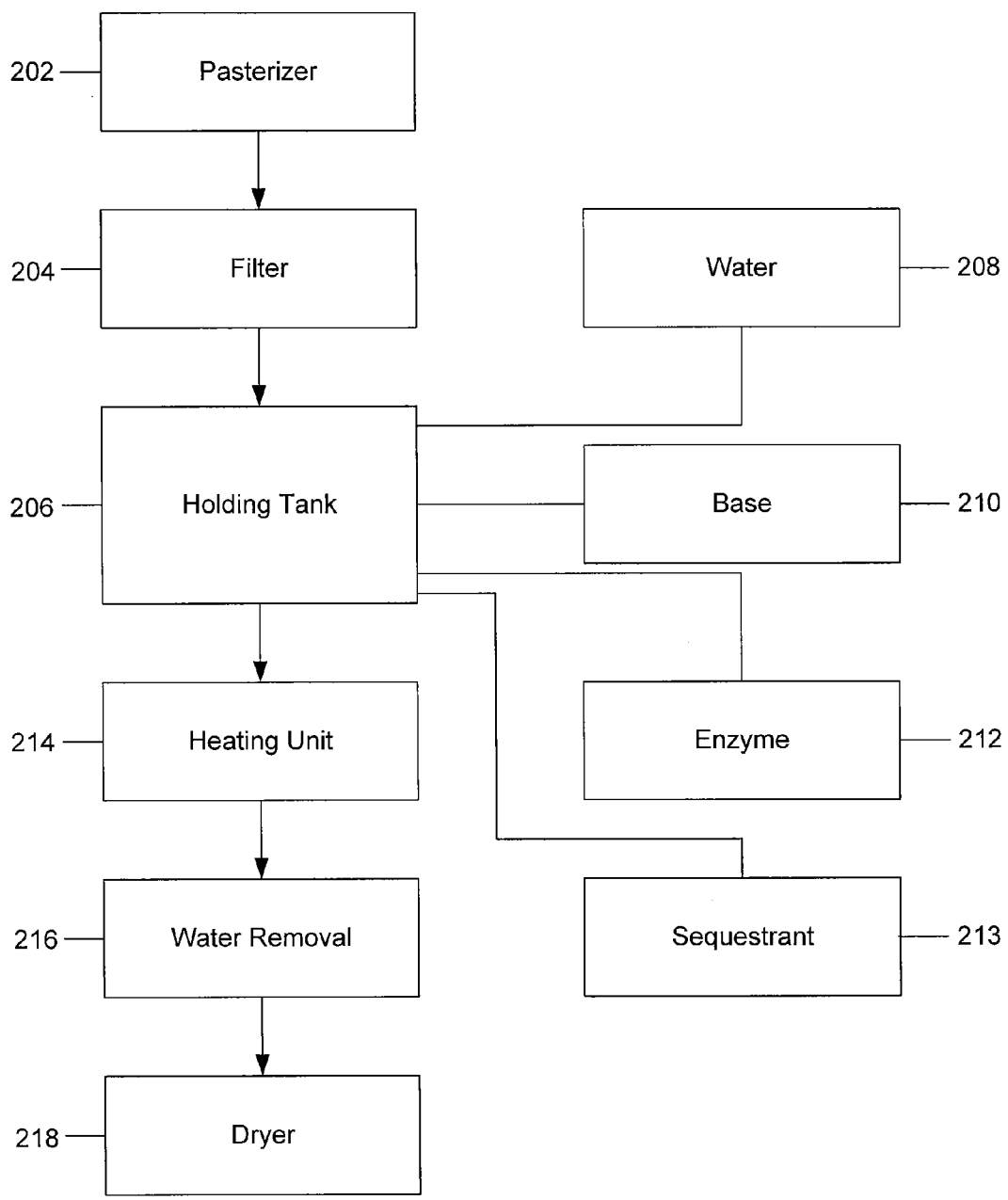
FIG. 2 illustrates an example of an apparatus for making protein hydrolysates according to embodiments of the invention.

FIG. 2 shows a simplified schematic of an apparatus 200 for making protein hydrolysates according to embodiments of the invention. The apparatus 200 may include a pasteurizer 202 to pasteurize a native whey protein mixture derived from a dairy process (e.g., a cheese making process). The pasteurized whey protein mixture may be concentrated into a whey protein concentrate with filter 204 that separates the WPC from the aqueous permeate. Alternatively (or in addition) water in the whey protein mixture may be evaporated in an evaporator unit (not shown) to concentrate the whey protein.

The WPC is then placed in a holding tank 206 that may be temperature controlled. The holding tank 206 may be coupled to a number of ingredient sources, including a water source 208 for adding water to the holding tank. Ingredient sources may also include a base source 210 for the basic material (e.g., aqueous sodium hydroxide), a sequestrant source 213 for a sequestrant (e.g., tripotassium phosphate) that may be added to the tank, and an enzyme source 212 for the enzymes that may be added.

The WPC added to the holding tank may be diluted by adding water from the water source 208 and made basic by added the basic material from the base source 210. For example, water may be added to dilute the whey protein from an initial concentration of 80%, by wt., whey protein to about 25%, by wt., or less (e.g., about 20% by wt, about 15% by wt., about 5% by weight, etc.). The aqueous dilution may be accompanied (or followed) by the addition of the basic material from the base source 210 to raise the pH of the whey protein mixture. The basic material may be a concentrated aqueous solution of a strong base, such as concentrated sodium hydroxide. The basic material may also include a sequestrant, such as tripotassium phosphate. The basic material may be added until the measured pH of the whey protein mixture reaches a particular pH, such as about 10 or more (e.g., about 10.4).

Following the addition of the base material from the base source 210, the basic whey protein mixture may be held at low temperature (e.g., 45° F.) in holding tank 206 for a period of time (e.g., about 30 minutes to about 5 hours). The basic whey protein mixture may be mixed during the holding period. The protease enzymes may then be added from the enzyme source 212 to start a first phase of the protein hydrolysis. In this phase, the mixture of the basic whey protein mixture and the protease enzymes may be held in the holding tank 206 at reduced temperatures (e.g., less than about 50° F., about 45° F., etc.) for a period of about 24 hours or less (e.g., 10 hours). During this "cold incubation" phase, the activity of the protease enzymes may be substantially less than their peak rate of catalyzing the hydrolysis of the native protein chains.

Without intending to be bound to a particular theory of the reaction process, it is believed that performing the hydrolysis slower and at a relatively high pH opens the protein structure such that the protein is hydrolyzed at points closer to the mid-point of the native protein chain instead of around the outside of a normally globular protein, leaving behind otherwise insoluble protein cores. Consequently, the cold incubation favors the production of protein hydrolysates of roughly equal size (e.g., about half the size of the starting protein) over the production of long and short protein fragments. Statistically, the cold incubation activity appears to favor a hydrolysate distribution that looks more like a bell curve, compared to a more conventional, bi-modal population distribution with large populations of both large and small hydrolysate fragments.

Following the cold incubation in the holding tank 206, the temperature of the tank may be adjusted to a higher temperature (e.g., about 120° F.) for a shorter period of time (e.g., about 2 hours or less, about 40 minutes, etc.) for a "warm incubation" hydrolysis phase. In this phase, the activity of the protease enzymes are at (or approaching) peak catalysis rates. The warm incubation increases the amount of native protein and larger protein hydrolysates that are hydrolyzed into the desired fragment range (e.g., about 2000 to 5000 Daltons).

At the end of the warm incubation phase, the protein hydrolysates mixture may be transported from the holding tank 206 to a heating unit 214 where the mixture is raised to a temperature (e.g., about 180° F. or more, about 190° F., etc.) that inactivates the protease enzyme and stops the protein hydrolysis reaction. The heating unit 214 may include one or more bent, twisted, and/or coiled conduits in thermal contact with a heat source (e.g., heated water, steam, heating coils, etc.). The protein hydrolysates mixture passes through the conduit to rapidly equilibrate the temperature of the mixture with the heat source. In some examples, the pasteurizer 202 may also be used as the heating unit 214 to inactivate the protease enzymes.

The pH of the hydrolyzing mixture may also be monitored during the cold and warm incubations. A pH meter (not shown) may be placed in the holding tank 206 to provide periodic or constant measurements of the mixture's pH. Because protein hydrolysis forms a carboxylic acid group on one of the protein hydrolysates, the pH of the basic whey protein mixture will drop from above 10 to about 9.5 or less. The pH drop may accelerate during the warm incubation when carboxylic acid groups are being formed at a faster rate. In some embodiments, the pH may be used as an indicator for when the cold incubation phase should be terminated. For example, when the pH of the hydrolyzing mixture falls below 9.5, the cold incubation phase may end regardless of the time. In other embodiments, the cold incubation phases may last for a predetermined period of time.

Following the high-temperature inactivation of the protease enzymes, the protein hydrolysates mixture may be concentrated. Concentrating the hydrolysates may involve filtering the mixture through a filtration unit 216 to separate the hydrolysates in the retentate from aqueous components of the permeate. The hydrolysates mixture may also be concentrated with an evaporator (not shown) that evaporates water off the mixture.

The concentrated protein hydrolysates may then be dried in a drying unit 218. The drying unit 218 may be a spray dryer that atomizes the protein hydrolysates while exposing them to a warm, dry atmosphere that rapidly evaporates residual water and leaves a protein hydrolysates powder. The dried product may be packaged and stored until its ready for use as a protein additive in food making processes.

The protein source used in the description of the apparatus 200 was whey protein, but it should be appreciated that other proteins may be used with the apparatuses and methods for making protein hydrolysates. For example, apparatus 200 may be used with other dairy proteins such as casein, as well as proteins derived from soy, nuts, vegetables, and animals, among other food sources.

Examples of Foods Made with Protein Hydrolysates

Figure 3:
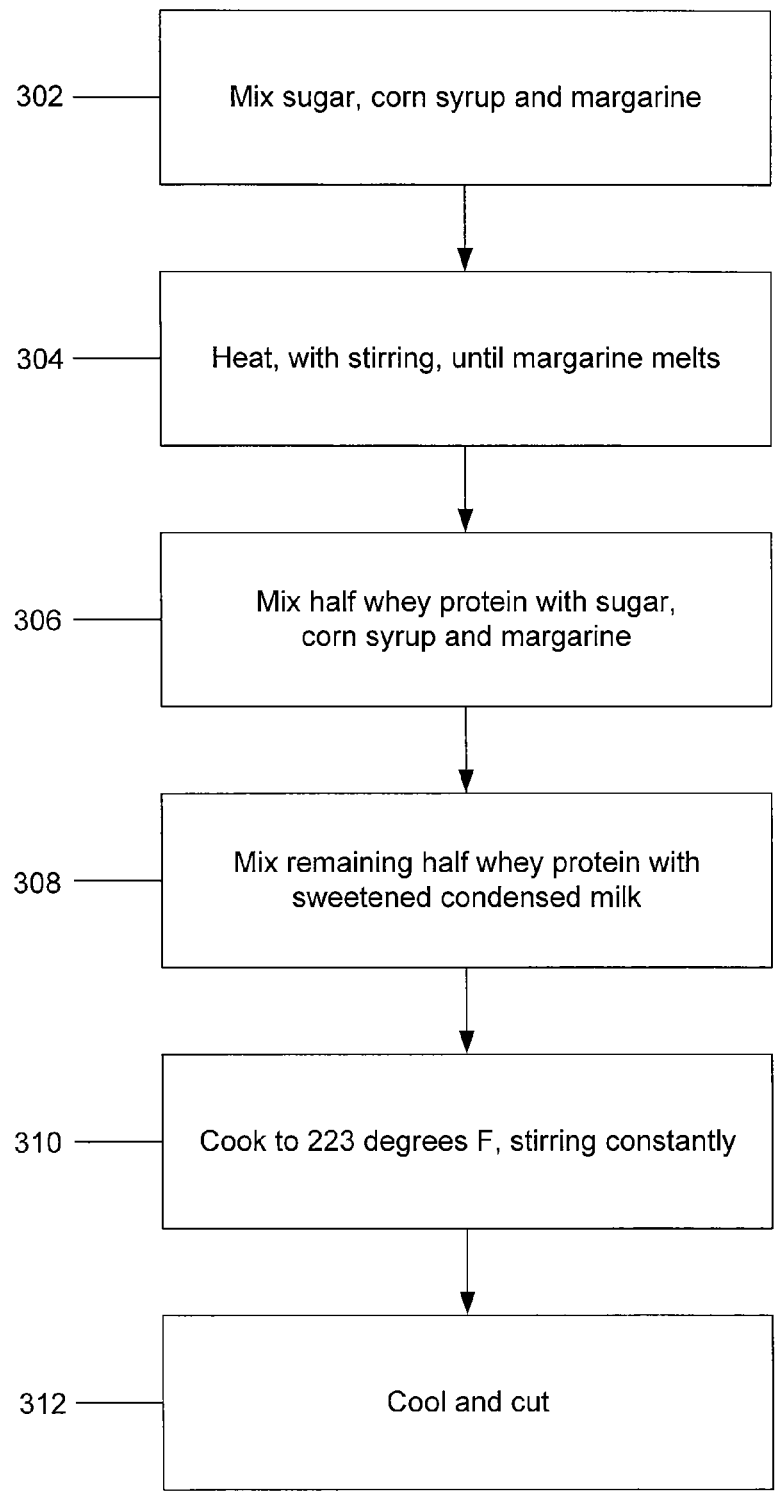
FIG. 3 is a flowchart that includes steps in a method of making a protein added confectionery with protein hydrolysates according to embodiments of the invention.

FIG. 3 shows a flowchart that includes steps in a method of making a protein added confectionery with protein hydrolysates according to embodiments of the invention. These confectioneries may include caramels, chocolates, fudges, taffies, nougats, gums, ice creams, protein/nutrition or meal replacement bars, and toffees, among others. For example, method 300 includes steps to make a protein added caramel confectionery with the protein hydrolysates. The method 300 may include mixing together ingredients including sweeteners such as sugar, corn syrup, etc., with butter or margarine 302. The ingredients may be heated and stirred until the butter and/or margarine melts 304.

The protein hydrosylates may be divided into two portions before being added to the melted ingredients. A first portion of the protein hydrolysates may be added directly to the melted ingredients 306 without first being premixed with other ingredients. A second portion of the hydrolysates may be mixed with additional ingredients 308, including sweetened condensed milk before being added to the rest of the melted ingredients. The mixture of all the ingredients may be allowed to cook 310 until the carmel product reaches a designated temperature (e.g., 223° F.), while the mixture is being stirred. After cooking, the mixture may be allowed to cool 312 so that the caramel product solidifies. The solid caramel may cut or otherwise formed into desired shapes (e.g., cubes, nuggets, bars, barrels, sheets, rolls, balls, etc.). Table 1 provides a list of ingredients, and their relative amounts by weight, used in one embodiment of the protein-fortified caramels.

TABLE 1

Ingredients for Exemplary Protein Fortified Caramels

| Ingredient | Weight Percentage |
|---|---|
| Granulated Sugar | 6.17% |
| Corn Syrup | 31.7% |
| Margarine | 10.7% |
| Whey Protein Hydrolysates | 14.0% |
| Sweetened Condensed Milk | 37.1% |
| Vanilla | 0.40% |

It should be appreciated that a variety of additional ingredients can be used in addition to (or in lieu of) those listed in Table 1. For example, the granulated sugar and corn syrup can be supplemented or replaced by other types of sweeteners. The margarine can be supplemented or replaced by butter. Additional flavorings may be used in addition to, or as a replacement for the vanilla. The relative amounts of the ingredients may also be varied.

Figure 4:
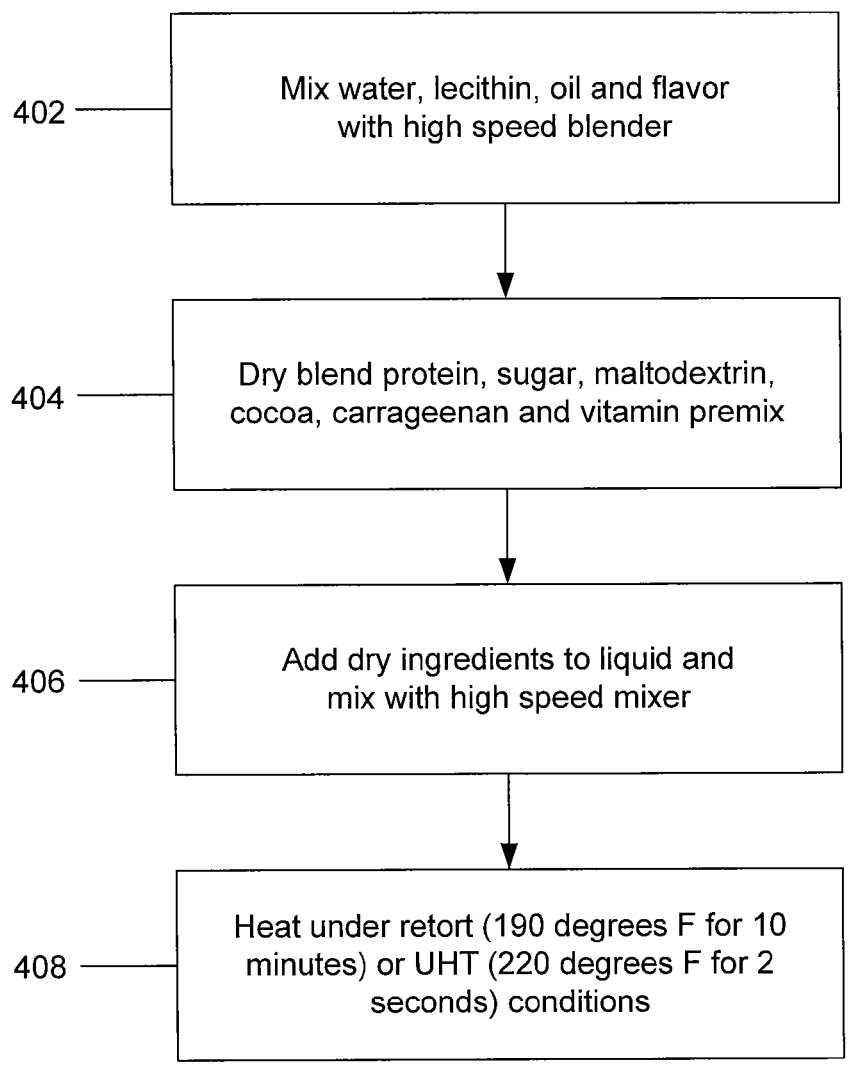
FIG. 4 is a flowchart showing steps of making a protein fortified beverage with protein hydrolysates according to embodiments of the invention.
Figure 5A:
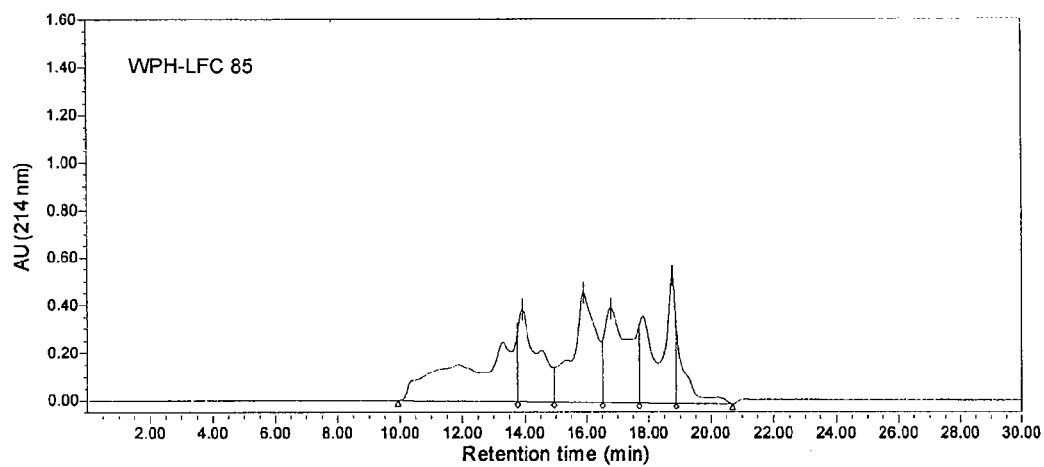
FIGS. 5A-F show graphs of HPSEC chromatograms of experimental runs of hydrolyzed proteins.
Figure 5B:
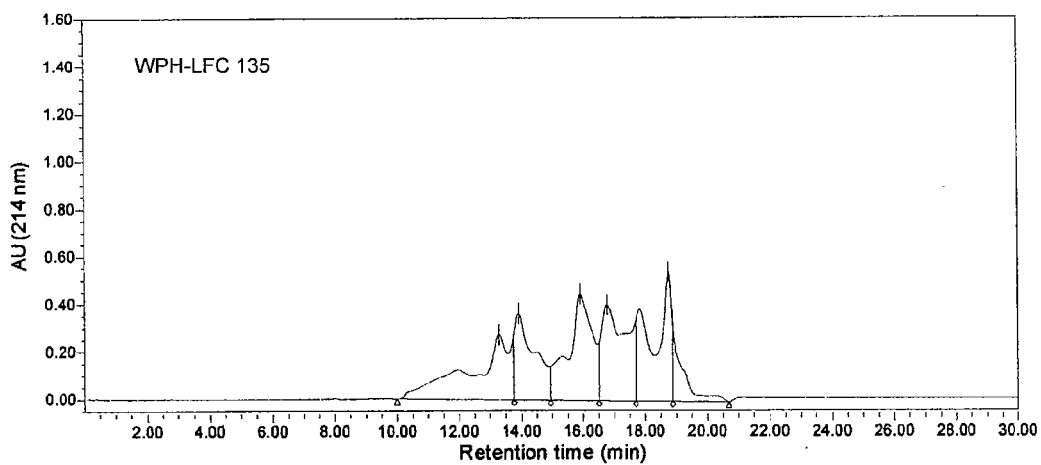
Figure 5C:
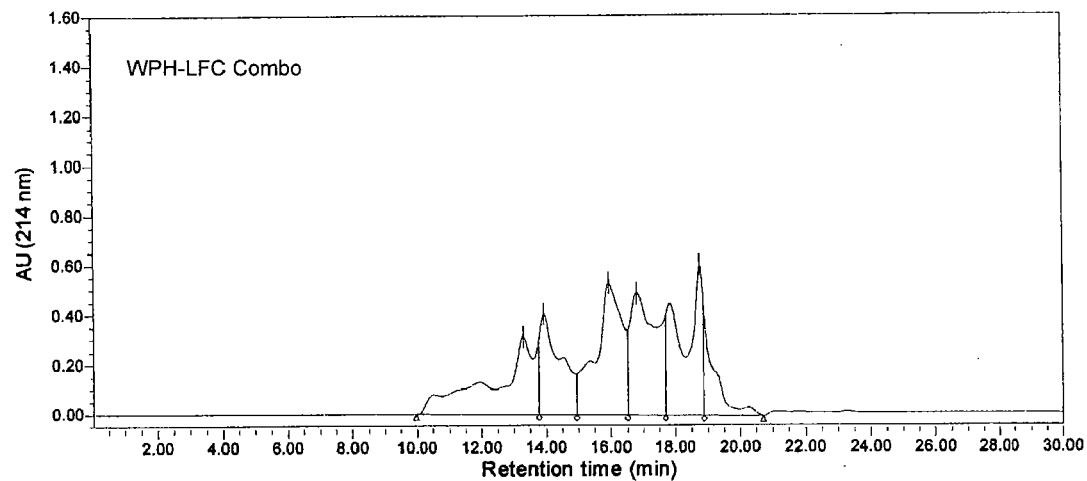
Figure 5D:
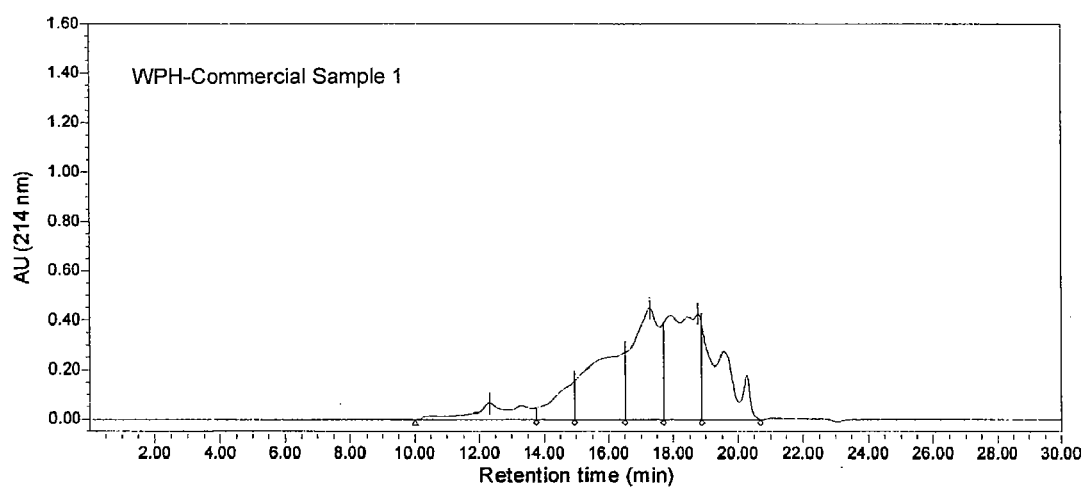
Figure 5E:
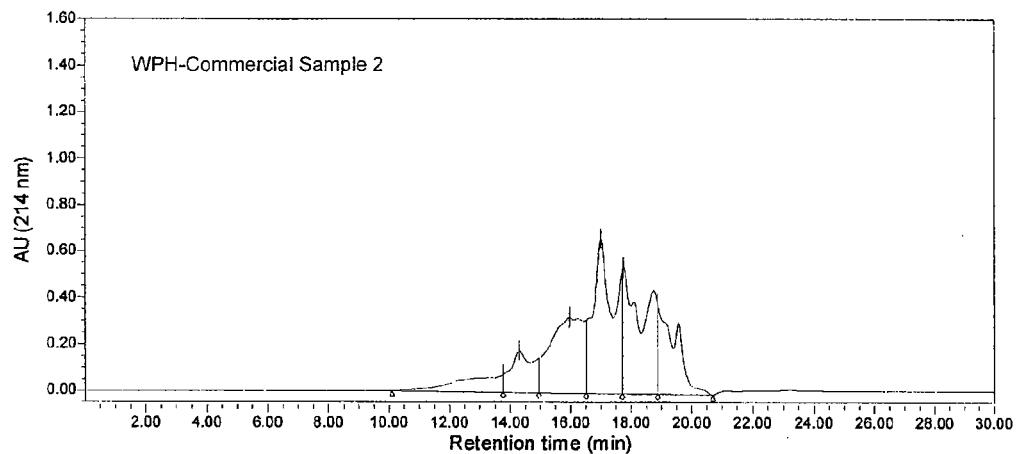
Figure 5F:
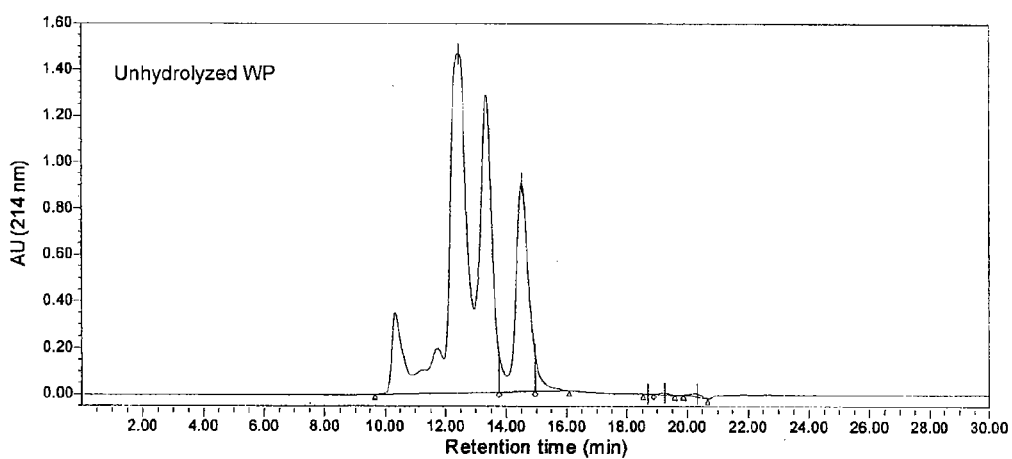

The protein added foods that may include the protein hydrolysates of the invention are not limited to solids. The hydrolysates may also be added to liquid beverages, including sodas, coffees, shakes, bottled water, sports drinks, fruit juices, infant formula, and dairy drinks, among other beverages. FIG. 4 shows a flowchart of a method 400 for making a protein-fortified beverage that includes protein hydrolysates according to embodiments of the invention. The method 400 may include mixing ingredient, which may include water, lecithin, oil, and flavorings among other ingredients, in a high-speed blender 402. The method may also include dry blending 404 the protein hydrolysates, sugar, maltodextrin, cocoa, carrageenan, and vitamins, among other dry ingredients. The liquid mixture may be added to the dry mixture in a high-speed blending process 406. The mixture of liquid and dry ingredients may also be heated 408. Examples of the heating step may include heating the mixture at a temperature of about 190° F. for about 10 minutes. Examples also include having the mixture undergo an ultra-high temperature (UHT) heating process where the mixture is heated to about 220° F. for a short period of time (e.g., 2 seconds). Table 2 provides a list of ingredients, and their relative amounts by weight, used in one embodiment of the protein-fortified beverage.

TABLE 2

Ingredients for Exemplary Protein Fortified Beverage

| Ingredient | Weight Percentage |
|---|---|
| Water | 66.0% |
| Whey Protein Hydrolysates | 6.66% |
| Sugar | 9.20% |
| Maltodextrin (10 DE) | 9.20% |
| Canola Oil | 6.00% |
| Dutch Cocoa | 0.80% |
| Soy Lecithin | 1.00% |
| Flavoring Agents | 0.20% |
| Carrageenan | 0.05% |
| Vitamins | 0.91% |

As with the protein added caramel ingredients above, it should be appreciated that a variety of additional ingredients can be used in addition to (or in lieu of) those listed in Table 2. For example, the sugar can be supplemented or replaced by other types of sweeteners. The canola oil can be supplemented or replaced by other types of oils. Additional ingredients may also be added to enhance the flavor, texture, and/or viscosity of the beverage. Alternatively, acidulants may be added to create a low pH fruit based beverage, for example, an orange, lemon, or citrus blend beverage. The relative amounts of the ingredients may also be varied.

It should also be appreciated that the protein added foods made in the examples above is not an all inclusive list of foods that can be protein fortified with the protein hydrolysates of the invention. It is contemplated that the hydrolysates may be added to, for example, cheeses, breads, pastas, soups, pastries, cereals, rice, and many other varieties of foods.

EXPERIMENTAL

Example 1

Protein Hydrolysates Derived from Native Whey Protein

Protein hydrolysates are made from whey protein concentrate (WPC) that is a by-product of mozzarella cheese making. The process starts with 80%, by wt., WPC that is concentrated using ultrafiltration from the raw whey mixture separated from cheese curd. The 80% WPC is transferred to a temperature controlled holding tank where its is mixed with water to make a 10.3%, by wt., diluted whey protein solution. The holding tank can hold a 1000 lb batch of the protein hydrolysates mixture, where 128.75 lbs of the 80% WPC (i.e., 12.875% solids) is mixed with water to form the diluted whey protein solution.

The diluted whey protein solution is then made basic by adding sodium hydroxide to the holding tank. Preparation of the NaOH starts with diluting the concentration of a 40%, by wt., aqueous solution of NaOH to 20% NaOH with before adding the base to the diluted whey protein solution. For the 1000 lb batch, 15 lbs of the 40% NaOH is used to raise the pH of the whey mixture to 10.45. The pH is measured by first allowing adequate time for full incorporation of the base, then sampling and reading the pH using a pH meter. The basic whey protein solution sits in the holding tank at about 45° F. or less, for 5 hours before the addition of the protease enzymes.

Addition of the protease enzymes starts the cold incubation phase of the protein catalysis to form the protein hydrolysates. In this experiment, the protease enzyme is a neutral protease sourced from *Bacillus subtilis* and sold commercially under the tradename Protamex® by Noxozymes of Denmark. It is added to the basic whey protein mixture at a level of about 0.5% by wt. of the substrate. For the 1000 lb batch, about 0.515 lb of Protamex is added. The enzyme, which is shipped as a dry powder, is slurried in water before being added to the dilute whey protein mixture. It is soluble in water, and has a declared activity of 1.5 Anson units per gram, with optimum activity conditions including a pH of about 7.5 and temperature of around 50° C. (122° F.). It can be inactivated in 30 minutes at 50° C. (122° F.) or higher when the pH is 4, and can be inactivated in about 10 minutes at 85° C. (185° F.) or higher when the pH is 8.

The cold incubation phase lasts for 24 hours at 45° F. The protein hydrolysate products generated by the enzyme hydrolysis have terminal carboxylic acid groups that lower the pH of the mixture. At the end of 24 hours the measured pH of the mixture is about 9.5.

The mixture is then heated to 120-130° F. in a warm incubation phase that lasts for 70 minutes. At this incubation stage, enzyme activity is at its highest and the pH drops further. At the end of the 70 minutes, the enzymes are inactivated by heating the mixture to 195° F. for 10 minutes. Inactivation can also be done in a UHT step by heating the mixture to 250° F. for 2 seconds. The protein hydrolysate is then spray dried to separate more water and produce a powdered product.

Molecular weight profiles of the samples are determined by high pressure size exclusion chromatography (HPSEC). Protein hydrolysate samples are first rehydrated in MilliQ water (2.5 mL) for 30 minutes, and then diluted in a 1:1 ratio with the mobile phase and centrifuged at 13,500×g for 3 minutes. Supernatants are filtered through a 0.22 μm PVDF membrane before being injected onto the column (approx. 1% protein). The total area of the chromatograms are integrated and separated into six molecular weight ranges expressed as a percentage of the total surface (i.e., >10 kDa, 5-10 kDa, 2-5 kDa, 1-2 kDa, 0.5-1 kDa, and <0.5 kDa). Table 3 lists additional conditions used in the HPSEC analysis:

TABLE 3

Conditions Used for the HPSEC Analysis of Protein Hydrolysates

| | |
|---|---|
| Column | TSK-GEL, G2000 SWXL (7.8 i.d. × 300 mm) from Tosoh Biosep LLC |
| Guard Column | TSK-GEL, Guard SWXL (6.0 i.d. × 40 mm) from Tosoh Biosep LLC |
| Mobile Phase | Water:ACN:TFA  30:70:0.1% (v/v) |
| Flow Rate | 0.6 ml/min (isocratically) |
| Final Concentration of the Sample | 1% protein |
| Detection | UV @ 214 nm |
| Injection Volume | 20 μl |
| Temperature | 28° C. |

The HPSEC chromatograms of the six samples are shown in FIGS. 5A-F, respectively, and the distribution of the hydrolysates molecular weights in the six size ranges are listed in Table 4 below.

TABLE 4

Molecular Weight Profiles of the Different Protein Hydrolysate Samples

| Sample | >10 kDa | 5-10 kDa | 2-5 kDa | 1-2 kDa | 0.5-1 kDa | <0.5 kDa |
|---|---|---|---|---|---|---|
| WPH-LFC 85 min | 25.16 | 13.94 | 20.52 | 17.86 | 17.02 | 5.48 |
| WPH-LFC 135 min | 21.22 | 13.80 | 20.87 | 19.01 | 19.06 | 6.03 |
| WPH-LFC combo | 19.99 | 13.08 | 21.57 | 20.07 | 18.65 | 6.65 |
| WPH-Commercial Sample 1 | 6.26 | 6.13 | 19.81 | 24.06 | 26.65 | 17.08 |
| WPH-Commercial Sample 2 | 6.47 | 8.05 | 21.67 | 26.16 | 23.74 | 13.91 |
| Unhydrolyzed Whey Protein | 78.07 | 20.03 | 1.51 | 0.02 | 0.10 | 0.28 |

The first three protein hydrolysate samples (i.e., WPH-LFC 85 min, WPH-LFC 135 min, and WPH-LFC combo) were made according to the methods of the present invention. The molecular weight profiles of these samples show the majority of the hydrolysates formed in the 1 to 10 kDa range, with an average molecular weight between 2000 and 5000 Daltons. These samples had excellent organoleptic qualities, and no detectable bitterness. Solutions of up to 15% protein in solution could also be heated to high temperatures (e.g., about 212° F. for 15 minutes at 15 psi) without clumping and otherwise denaturing, making them excellent candidates as a protein additive for a variety of foods.

The next two protein hydrolysate samples (i.e., the WPH Commercial Samples 1 and 2) were commercially available samples of protein hydrolysates for use as protein additives, made according to conventional methods. The molecular weight profiles of these samples showed, on average, more than double the percentage of the smallest hydrolysates having a molecular weigh of less than 0.5 kDa. The higher concentrations of these small hydrolysates hurt the organoleptic qualities of the samples, which both had a noticeably strong bitter taste. These commercial samples were also susceptible to high heat treatment and either gelled or precipitated.

Finally the last sample (i.e., unhydrolyzed whey protein) was a comparative sample of the native WPC used in the protein hydrolysis process. The majority of this sample distribution was concentrated in the highest molecular weight category of greater than 10 kDa. No bitterness was detected in the native WPC sample, but as expected, it underwent considerable denaturing when heated.

The molecular weight profiles described above are more accurate predictors of the bitterness and other organoleptic qualities of the protein hydrolysates than just measuring the percentage degree of protein hydrolysis (i.e., % DH). A degree of hydrolysis measurement normally measures the extent to which target peptide bonds are broken in a protein by a hydrolysis reaction. But a DH of 50% does not necessarily mean that half the starting proteins were hydrolyzed. Instead it means that 50% of the peptide bonds that could be hydrolyzed by a particular protease enzyme have been hydrolyzed. Furthermore, the % DH value does not give any indication of the size of the resulting hydrolysates fragments. As discussed above, a catalytic protein hydrolysis process that produces a lot of small hydrolysates fragments has a much higher probability having a bitter taste.

Example 2A

LFC-WPH Protein Hydrolysates Derived from Native Whey Protein

Protein hydrolysates are made from whey protein concentrate (WPC) that is a by-product of mozzarella cheese making. The process starts with sweet whey that is concentrated using ultrafiltration to form an 80% whey protein retentate. The 80% whey protein retentate is transferred to a temperature controlled holding tank where it is mixed with water to make a 10.3%, by wt., diluted whey protein solution. The diluted whey protein solution contains about 9532 pounds of unhydrolyzed whey solids.

The diluted whey protein solution is then made basic by adding sodium hydroxide and tripotassium phosphate to the holding tank. To the holding tank 159 pounds of tripotassium phosphate are added, followed by sodium hydroxide until a pH of 10.5 is reached. The basic whey protein solution sits in the holding tank at about 45° F. or less, for 5 hours before the addition of the protease enzymes. The remaining steps in the hydrolysis reaction follow Example 1. The protein hydrolysates made according to this example were tested for heat stability and bitterness as the "LFC-WPH" sample.

Comparative Example 2B

NZDB Protein Hydrolysates

Protein hydrolysates were made according to a process described in U.S. Pat. No. 6,919,314, titled "Bioactive whey protein hydrolysate" to Schlothauer et al, and assigned to the New Zealand Dairy Board, the entire contents of which are herein incorporated by reference for all purposes. The process of making these protein hydrolysates (the "NZDB hydrolysates") started with a 10% (wt.) solution of whey protein concentrate that was adjusted to a pH of 7.0 with sodium hydroxide (NaOH). The neutral solution was then heated to a temperature of 122° F. before adding the protease enzyme Neutrase until an enzyme concentration of 0.3% (wt.) was reached.

The whey protein and protease enzyme solution was allowed to react for 1 hour before the pH was lowered to 5.0 with the addition of phosphoric acid. The temperature of the solution was then raised to 149° F. for 30 minutes and water removed to produce the protein hydrolysates product (referred to as the "NZDB hydrolysates").

Example 3

Protein Hydrolysates Bitterness Measurements

Measurements were made to quantify the bitterness of whey protein hydrolysates made by the processes described in Examples 2A&B, as well as for some commercially available protein hydrolysates (i.e., Hilmar 8350, and Hilmar 8390 made by Hilmar Ingredients, Hilmar, Calif.; and Biozate 1 made by Davisco Foods International, Inc, Eden Prairie, Minn.). The bitterness levels of the samples were quantified based on concentration equivalents of quinine hydrochloride in unhydrolyzed protein solutions. Increasing the concentration of the quinine increases the bitterness of the unhydrolyzed protein solution, so protein hydrolysates solutions found equivalent in bitterness to more concentrated quinine solutions are quantifiably more bitter than hydrolysates equivalent to less concentrated quinine solutions.

Aqueous solutions containing 7.5% (by wt.) of protein hydrolysates were tested for sensory evaluation against aqueous solutions of 7.5% (by wt.) of the unhydrolyzed protein that also contained quinine hydrochloride in discrete amounts from 0 to 0.03 mg/ml. Sensory panels were conducted over 5 days (one hydrolysate sample per day). Panelists were asked to taste the whey protein hydrolysate sample and then identify which of the quinine hydrochloride samples best matched the level of bitterness in the hydrolysate sample. The weighted average from each panel quantified the equivalent quinine hydrochloride concentration that corresponds to each whey protein hydrolysate sample. Table 5 shows the results of this sensory panel. The lower the quinine hydrochloride equivalent the less bitter the protein hydrolysate.

TABLE 5

Bitterness Profiles of Whey Protein Hydrolysates

| Protein Hydrolysates Source | Protein Hydrolysate Concentration, by weight, in Aqueous Solution | Weighted Average of Quinine Hydrochloride Equivalent (mg/ml) |
|---|---|---|
| LFC-WPH | 7.5% | $5.63 \times 10^{-3}$ |
| Hilmar 8350 | 7.5% | $33.33 \times 10^{-3}$ |
| Hilmar 8390 | 7.5% | $220.0 \times 10^{-3}$ |
| NZBD Hydrolysates | 7.5% | $5.94 \times 10^{-3}$ |
| Biozate 1 | 7.5% | $107.5 \times 10^{-3}$ |

At an equivalent concentration of 7.5%, by wt., the hydrolysates differed significantly in their bitterness level. The LFC-WPH protein hydrolysates made according to Example 2A were several times less bitter than the Hilmar 8350, Hilmar 8390, and Biozate 1 protein hydrolysates at the same concentration. Only the NZDB hydrolysates sample had a comparable level of bitterness to the LFC-WPH hydrolysates.

Additional bitterness measurements were made at varying concentrations of whey protein hydrolysates. Bitterness levels were quantified for protein hydrolysates solutions made from aqueous starting whey protein solutions that were 7%, 10%, 13%, and 16%, by wt., whey protein. The protein hydrolysates samples made from these solutions were compared to aqueous solutions of hydrochloride ranging from 0.005 to 0.73 mg/ml. Panelists were asked to taste the whey protein hydrolysate samples and then identify which of the quinine hydrochloride samples best matched the protein hydrolysate sample at each starting protein concentration. Results of this sensory analysis are depicted in Table 7.

TABLE 7

Bitterness of Protein Hydrolysates at Various Protein Concentrations

| Sample | % Protein (wt.) | Quinine Hydrochloride Equivalent Bitterness (mg/ml) |
|---|---|---|
| WPH-LFC | 7 | 0.005 |
| WPH-LFC | 10 | 0.007 |
| WPH-LFC | 13 | 0.01025 |
| WPH-LFC | 16 | 0.01575 |
| NZDB Hydrolysates | 7 | 0.0055 |
| NZDB Hydrolysates | 10 | 0.0065 |
| NZDB Hydrolysates | 13 | 0.009 |
| NZDB Hydrolysates | 16 | 0.014 |
| Biozate 1 | 7 | 0.061 |
| Biozate 1 | 10 | 0.0755 |
| Biozate 1 | 13 | 0.1095 |
| Biozate 1 | 16 | 0.151 |
| Hilmar 8350 | 7 | 0.031 |
| Hilmar 8350 | 10 | 0.0445 |
| Hilmar 8350 | 13 | 0.055 |
| Hilmar 8350 | 16 | 0.0685 |
| Hilmar 8390 | 7 | 0.174 |
| Hilmar 8390 | 10 | 0.197 |
| Hilmar 8390 | 13 | 0.256 |
| Hilmar 8390 | 16 | 0.2945 |

Table 7 shows that the bitter flavor of the hydrolysates increased with increasing protein concentration in the initial solution. Only two of the samples, WPH-LFC and NZDB Hydrolysates, had bitterness levels that were low enough to be acceptable for consumption at all protein concentrations tested. The remaining hydrolysate samples were too bitter, even at the 7% protein concentration, to be acceptable additives in beverages, nutritional bars or other kinds of food products or supplements. Taste panelists also commented that except for the WPH-LFC and NZDB Hydrolysates samples, the protein hydrolysates had brothy and "wet dog" flavors and odors that would also make them undesirable as food or beverage additives. In addition, while the NZDB Hydrolysates sample had a comparable taste to the WPH-LFC sample, it had an undesirable level of chalkiness.

Example 4

Protein Hydrolysates Heat Stability Measurements

The heat stability of various whey protein hydrolysates were measured. Commercial protein hydrolysate samples, whey protein hydrolysates made according to Example 2, Biozate 1 (Davisco Foods International, Inc, Eden Prairie, Minn.), and Hilmar Ingredients (Hilmar, Calif.) were solubilized to various protein concentrations in distilled room temperature water (see Table 6). 10 ml samples of the solubilized protein hydrolysates were dispensed into vials (Bellco Glass 18×150 mm), sealed with a 20 mm septum stopper, and secured with an aluminum seal using a 20 mm crimper. Vials were submerged in an oil bath (Lauda Proline series PV15c) set at 255° F. Vials were removed from the oil bath at specified times (10, 20, 30, and 40 minutes) and immediately placed in an ice bath to cool the sample. Thirty minutes after completing the heat treatment all samples were examined for signs of protein precipitation, gelling and coagulation. The heat stability results are presented in Table 6.

TABLE 6

Heat Stability of Commercial Hydrolysate Samples

| Sample | Protein Conc. (% wt.) | 10 minutes | 20 minutes | 30 minutes | 40 minutes |
|---|---|---|---|---|---|
| WPH-LFC | 7 | Pass | Pass | Pass | Pass |
| WPH-LFC | 10 | Pass | Pass | Pass | Pass |
| WPH-LFC | 13 | Pass | Fail | Fail | Fail |
| WPH-LFC | 16 | Fail | Fail | Fail | Fail |
| Hilmar 8350 | 7 | Pass | Pass | Fail | Fail |
| Hilmar 8350 | 10 | Pass | Fail | Fail | Fail |
| Hilmar 8350 | 13 | Fail | Fail | Fail | Fail |
| Hilmar 8350 | 16 | Fail | Fail | Fail | Fail |
| Hilmar 8390 | 7 | Fail | Fail | Fail | Fail |
| Hilmar 8390 | 10 | Fail | Fail | Fail | Fail |
| Hilmar 8390 | 13 | Pass | Pass | Fail | Fail |
| Hilmar 8390 | 16 | Pass | Fail | Fail | Fail |
| NZDB | 7 | Fail | Fail | Fail | Fail |
| NZDB | 10 | Fail | Fail | Fail | Fail |
| NZDB | 13 | Fail | Fail | Fail | Fail |
| NZDB | 16 | Fail | Fail | Fail | Fail |
| Biozate 1 | 7 | Pass | Pass | Pass | Pass |
| Biozate 1 | 10 | Pass | Pass | Pass | Pass |
| Biozate 1 | 13 | Pass | Pass | Fail | Fail |
| Biozate 1 | 16 | Pass | Fail | Fail | Fail |

Table 6 shows that many of the commercially available protein hydrolysate samples are not heat stable at commercial heat processing conditions. This data further shows that the protein hydrolysates prepared according to Example 2A, above (listed as the "WPH-LFC" sample in Table 6) is heat stable over a wide range of protein concentrations and heating times. Only the Biozate 1 sample showed comparable heat stability to protein hydrosylates according to embodiments of the invention. This may be explained by the fact that the Biozate 1 sample is derived from a whey protein isolate (>90% protein), and thus lacks the minerals that can reduce the heat stability of the protein hydrolysates. The protein hydrolysates prepared according to Example 2A can achieve the same level of heat stability without having to remove the minerals present in the native whey protein starting materials.

Example 5

Chromatographic Signatures of the Whey Protein Hydrolysates

Samples of Unhydrolyzed WPC (Leprino Foods, Denver, Colo.), LFC-WPH, Biozate 1 (Davisco Foods International, Inc, Eden Prairie, Minn.), NZDB Hydrolysates, and Hilmar Ingredients (Hilmar, Calif.) were run through a capillary electrophoresis ("CE") instrument to obtain sample profiles. All but the regular WPC was hydrolyzed. The CE profile of each sample was obtained using a P/ACE™ MDQ Capillary Electrophoresis System controlled by System Gold software (Beckman, Fullerton, Calif., USA) using an IBM NetVista computer (IBM Corp., Armonk, N.Y., USA). An uncoated fused-silica capillary column of 72 cm effective length, 50 μm ID (Beckman, Fullerton, Calif., USA) was assembled in the P/ACE cartridge. Sample (3 mg/mL) solutions from the hydrolysates were prepared in de-ionized water and filtered through 0.22 μm Acrodisc® filters (Pall Corp., Ann Arbor, Mich., USA) prior to injection at 1 psi of pressure for 15 seconds. The running sodium phosphate buffer (0.1 M, pH 2.5) was obtained from Sigma-Aldrich (St. Louis, Mo., USA). The CE analyses were performed for a total duration of 60 min at a constant voltage (27 kV) and temperature (25° C.) using a UV-detection at 214 nm. The CE chromatograms are shown in FIGS. 6A-F.

Figure 6A:
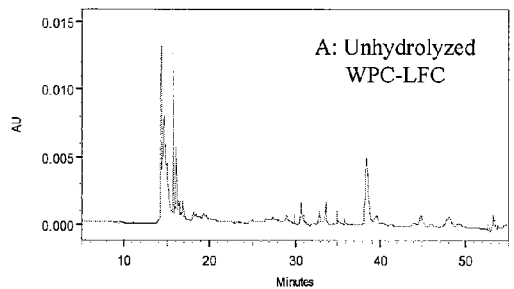
FIGS. 6A-F show comparative capillary electrophoresis graphs of protein hydrolysis samples.
Figure 6B:
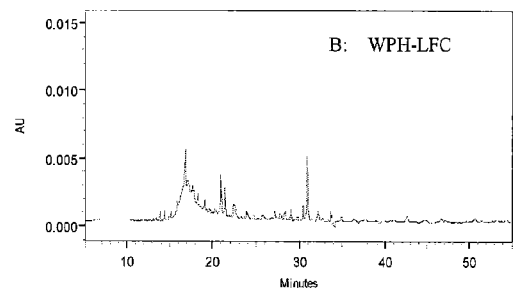
Figure 6C:
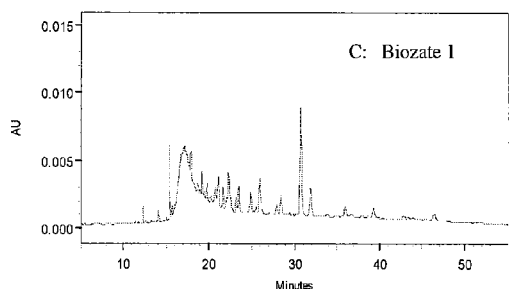
Figure 6D:
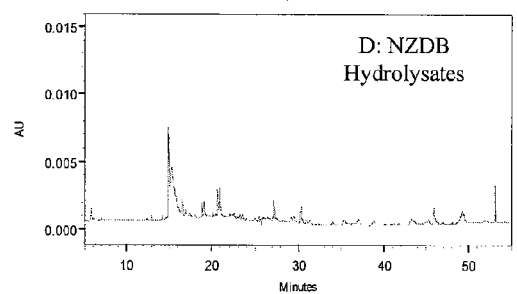
Figure 6E:
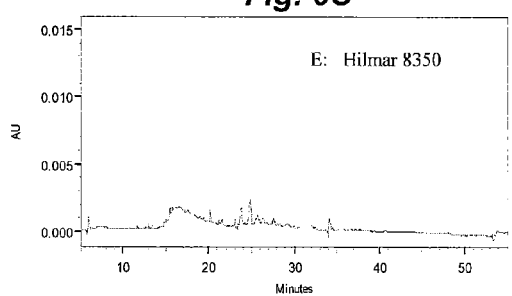
Figure 6F:
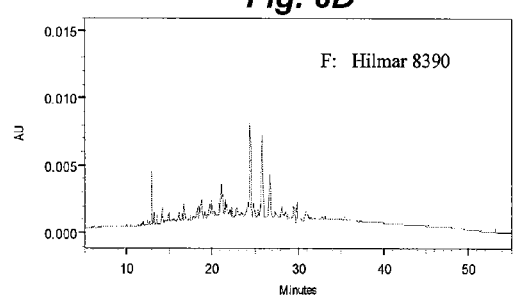

FIG. 6A shows the CE chromatogram for an unhydrolyzed whey protein concentrate. FIG. 6B shows the CE chromatogram for protein hydrolysates made according to Example 2A above. FIGS. 6C-F show comparison CE chromatograms of the NZDB and commercially available protein hydrolysates: FIG. 6C shows the chromatogram for the Biozate 1 protein hydrolysates; FIG. 6D is the chromatogram for the NZDB protein hydrolysates; and FIGS. 6E & F are the chromatograms for the Hilmar 8350 and 8390 protein hydrolysates, respectively. The chromatograms show that protein hydrolysates samples have significantly different product profiles, which may be correlated to their different bitterness and heat stability properties (among other properties). While not wishing to be bound to a particular theory, it has been suggested that the hydrolysis of specific whey protein constituents is responsible for most of the bitterness in whey protein hydrolysates products. The starting whey protein is a mixture of proteins that include beta-lactoglobulin, alpha-lactalbumin, and serum albumin, among other proteins. It is believed that hydrolysates of the alpha-lactalbumin are significantly bitter, and that hydrolysis processes that favor the hydrolysis of other starting whey proteins (e.g., beta-lactoglobulin) will produce less bitter protein hydrolysis samples. Thus, the variation in bitterness of the protein hydrolysate samples studied may be due, at least in part, to the relative extent of hydrolysis between the alpha-lactalbumin and beta-lactoglobulin starting proteins.

The data from the above examples show that protein hydrolysates according to embodiments of the invention (e.g., the WPH-LFC sample) has both a low-bitterness/desirable flavor profile and high heat stability for a variety of heat processing applications. In contrast, NZDB hydrolysates sample had poor heat stability, while the Biozate 1 sample tested highly bitter across all the measured protein concentrations. The Hilmar protein hydrolysates exhibited both poor heat stability and high bitterness, in addition to other brothy flavors.

Figure 7:
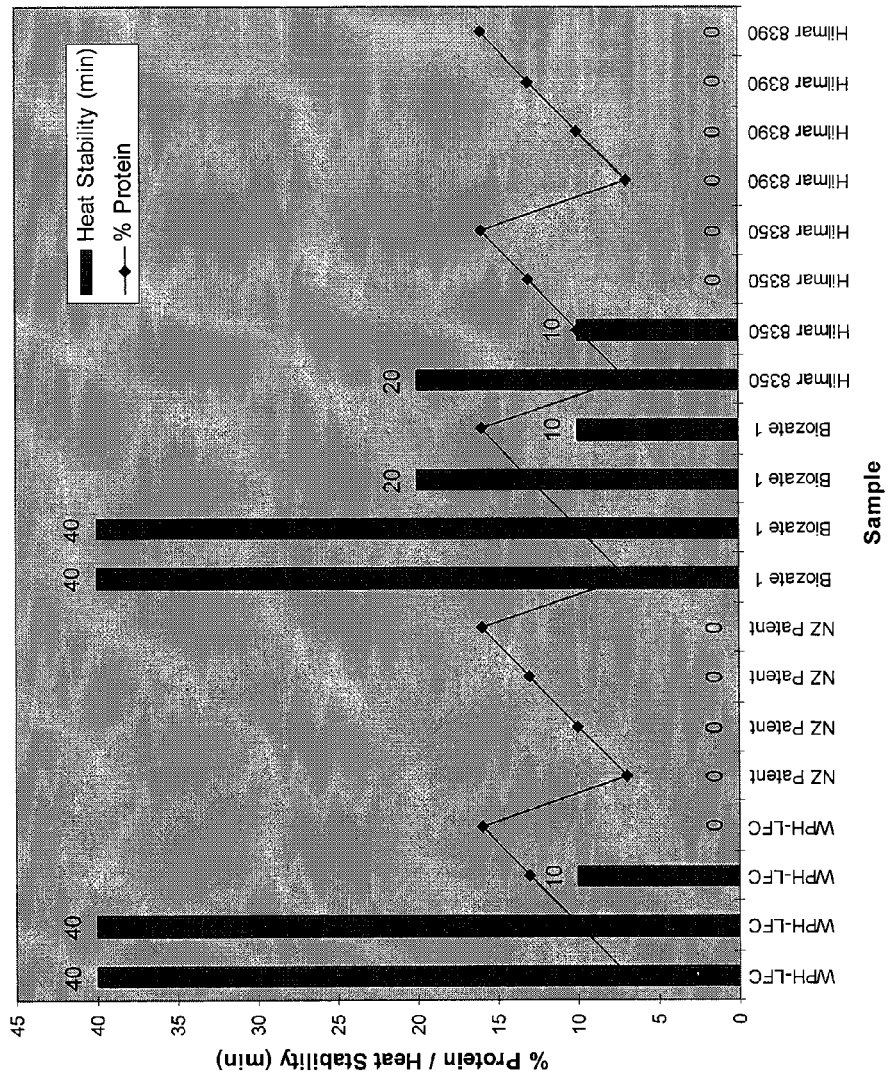
FIG. 7 shows a graph of the effect of protein concentration on heat stability for various protein hydrolysates samples.

FIGS. 7 and 8 bring this data together showing that the inventive hydrolysate product has a combination of high heat stability and low bitterness that is not found in the other protein hydrolysates samples. FIG. 7 shows a graph of the effect of protein concentration on heat stability for various protein hydrolysates samples. while FIG. 8 shows a graph of the effect of protein concentration on bitterness for various protein hydrolysates samples. Together FIGS. 7 and 8 shows that the LFC-WPH protein hydrolysates sample had a heat stability of greater than 10 minutes at 255° F. and a bitterness, as measured by equivalent of quinine hydrochloride of less than 0.03 mg/ml.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of making protein hydrolysates, wherein the method comprises:
   providing a solution comprising at least one dairy protein;
   adjusting the pH of the solution to about 10.4 or more to form a basic protein solution, cooling the basic protein solution by adjusting the temperature of the solution to about 50° F. or less; and
   adding a protease enzyme to the basic, cooled protein solution, wherein the protease enzyme converts at least a portion of the dairy protein to dairy protein hydrolysates having a weight average molecular weight of about 1000 to about 10,000 Daltons.

2. The method of claim 1, wherein the adjusting of the pH of the solution comprises adding a strong base to the solution.

3. The method of claim 2, wherein the strong base comprises sodium hydroxide.

4. The method of claim 1, wherein the adjusting of the pH of the solution comprises adding a sequestrant to the solution.

5. The method of claim 4, wherein the sequestrant comprises phosphates, pyrophosphates, diphosphates, triphosphates, polyphosphates, carbonates, or citrates.

6. The method of claim 4, wherein the sequestrant comprises disodium diphosphate, trisodium diphosphate, tetrasodium diphosphate, dipotassium diphosphate, tetrapotassium diphosphate, dimagnesium diphosphate, pentasodium triphosphate, pentapotassium triphosphate, sodium polyphosphate, potassium polyphosphate, ammonium polyphosphate, potassium tripolyphosphate, disodium phosphate, dipotassium phosphate, citric acid, lactobionic acid, phosphoric acid, tetrasodium pyrophosphate, sodium metaphosphate, sodium hexametaphosphate, tripotassium phosphate, trisodium citrate, trisodium phosphate, tripotassium citrate, disodium pyrophosphate, disodium ethylenediaminetetraacetate, sodium gluconate, sodium lactobionate, sodium potassium tripolyphosphate, sodium hexametaphosphate, potassium tripolyphosphate, or tetrasodium pyrophosphate.

7. The method of claim 1, wherein the basic protein solution is mixed for about 1 hour or more before the addition of the protease enzyme.

8. The method of claim 7, wherein the basic solution is mixed for about 5 hours before the addition of the protease enzyme.

9. The method of claim 1, wherein the protease enzyme comprises a non-alkaline protease enzyme.

10. The method of claim 1, wherein the protease enzyme comprises a neutral protease enzyme.

11. The method of claim 1, wherein the protease enzyme comprises a *Bacillus* sourced protease enzyme.

12. The method of claim 1, wherein the adding of the protease enzyme comprises adding the protease enzyme in an amount that is about 0.5% by weight of the protein in the basic protein solution.

13. The method of claim 1, wherein the basic protein solution is mixed for about 30 minutes or more after the protease enzyme is added.

14. The method of claim 1, wherein the basic protein solution containing the protease enzyme is incubated until the pH is reduced to about 9.5 or less.

15. The method of claim 1, wherein the method comprises incubating the protease enzyme containing basic protein solution at about 90° F. to about 140° F.

16. The method of claim 15, wherein the incubation period is about 30 to about 300 minutes.

17. The method of claim 1, wherein the method comprises heating the basic protein solution to about 180° F. after the protease enzyme is added to inactivate the protease.

18. The method of claim 17, wherein the solution is heated to about 180° F. for about 10 minutes.

19. The method of claim 1, wherein the method comprises:
   removing water from the protein hydrolysates containing solution to form a protein hydrolysate concentrate; and
   drying the precipitate to form a dry powder comprising the protein hydrolysates.

20. The method of claim 1, wherein the protein comprises about 1% wt. or more of the solution.

21. The method of claim 1, wherein the protein hydrolysates are heat stable in retort or UHT conditions at a protein level of up to 18% in solution.

22. A method of making protein hydrolysates, wherein the method comprises:
   providing a solution comprising at least one dairy protein;

cooling the solution by adjusting the temperature of the dairy protein solution to about 50° F. or less;
adjusting the pH of the solution to about 8 or more; and
adding a protease enzyme to the cooled, basic protein solution, wherein the protease enzyme converts at least a portion of the protein to dairy protein hydrolysates having a weight average molecular weight of about 1000 to about 10,000 Daltons.

23. A method of making whey protein hydrolysate, the method comprising:
   (a) providing a solution comprising about 1% by wt. of whey protein concentrate;
   (b) adjusting the temperature of the solution to about 45° F.;
   (c) adjusting the pH of the solution to about 10.4 by adding a pH adjuster selected from the group consisting of a strong base, a sequestrant, and a mixture of a strong base and a sequestrant;
   (d) mixing the solution at the 45° F. temperature;
   (e) adding a protease enzyme to the solution, wherein the protease enzyme is added in an amount of about 0.5% by weight of the whey protein concentrate;
   (f) mixing the solution either for 24 hours or until the pH drops to about 9.5 or less, and wherein the protease enzyme converts at least a portion of the whey protein to whey protein hydrolysates having a weight average molecular weight of about 1000 to about 10,000 Daltons;
   (g) incubating the solution at about 90° F. to about 140° F. for about 30 to about 300 minutes;
   (h) heating the solution to about 180° F. for about 10 minutes to inactivate the protease;
   (i) removing water from the solution to form a concentrate; and
   (j) drying the concentrate to form a solid composition comprising the whey protein hydrolysate.

24. The method of claim 1, wherein the protein hydrolysates have a bitterness equivalent of about 0.03 mg/ml or less of quinine hydrochloride.

25. The method of claim 22, wherein the protein hydrolysates have a bitterness equivalent of about 0.03 mg/ml or less of quinine hydrochloride.

26. The method of claim 23, wherein the protein hydrolysates have a bitterness equivalent of about 0.03 mg/ml or less of quinine hydrochloride.

27. The method of claim 1, wherein the protein hydrolysates have a heat stability of about 190° F. or more for about 5 minutes of more.

28. The method of claim 22, wherein the protein hydrolysates have a heat stability of about 190° F. or more for about 5 minutes of more.

29. The method of claim 23, wherein the protein hydrolysates have a heat stability of about 190° F. or more for about 5 minutes of more.

* * * * *

UNITED STATES PATENT AND TRADEMARK OFFICE
CERTIFICATE OF CORRECTION

Page 1 of 1

PATENT NO. : 8,101,377 B2
APPLICATION NO. : 11/619957
DATED : January 24, 2012
INVENTOR(S) : Madison V. Blanton et al.

It is certified that error appears in the above-identified patent and that said Letters Patent is hereby corrected as shown below:

Column 22, line 20, claim 27, please delete "of" and insert --or--.

Column 22, line 23, claim 28, please delete "of" and insert --or--.

Column 22, line 26, claim 29, please delete "of" and insert --or--.

Signed and Sealed this
Third Day of April, 2012

David J. Kappos
*Director of the United States Patent and Trademark Office*